United States Patent
Lee et al.

(10) Patent No.: US 8,044,371 B2
(45) Date of Patent: Oct. 25, 2011

(54) SURFACE ACOUSTIC WAVE DEVICE AND METHOD FOR SIGNAL AMPLIFICATION OF SURFACE ACOUSTIC WAVE ELEMENT

(75) Inventors: Hun Joo Lee, Seoul (KR); Soosuk Lee, Suwon-si (KR); Kak Namkoong, Seoul (KR); Chinsung Park, Yongin-si (KR); Kieun Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 267 days.

(21) Appl. No.: 12/396,807

(22) Filed: Mar. 3, 2009

(65) Prior Publication Data
US 2010/0117004 A1 May 13, 2010

(30) Foreign Application Priority Data
Nov. 7, 2008 (KR) .................. 10-2008-0110553

(51) Int. Cl.
*G01T 1/04* (2006.01)
*G01J 1/58* (2006.01)
*H01J 40/14* (2006.01)
(52) U.S. Cl. .................. 250/473.1; 250/458.1; 250/215
(58) Field of Classification Search ............... 250/473.1, 250/458.1, 215, 306, 307, 483.1, 577
See application file for complete search history.

(56) References Cited

U.S. PATENT DOCUMENTS

| 6,379,969 | B1 | 4/2002 | Mauze et al. |
| 6,680,206 | B1 | 1/2004 | McDevitt et al. |
| 2003/0053936 | A1* | 3/2003 | Potyrailo et al. ........... 422/82.11 |
| 2006/0033039 | A1 | 2/2006 | Williams et al. |
| 2007/0018096 | A1* | 1/2007 | Kawakatsu ................... 250/309 |

FOREIGN PATENT DOCUMENTS
KR 1020050024783 A 3/2005

\* cited by examiner

*Primary Examiner* — David Porta
*Assistant Examiner* — Faye Boosalis
(74) *Attorney, Agent, or Firm* — Cantor Colburn LLP (57) ABSTRACT

A surface acoustic wave ("SAW") device including a SAW element, a first material, a luminescence material and a light source, and a method for signal amplification of a SAW element. The first material may be positioned on the SAW element and bound to a target material in a sample. The luminescence material may be bound to the target material. The light source may apply light to the luminescence material. The SAW device and the method for signal amplification of a SAW element using the same allow amplification of a signal of the SAW element by an electromagnetic wave generated when light is applied to the luminescence material.

20 Claims, 9 Drawing Sheets

SURFACE ACOUSTIC WAVE DEVICE AND METHOD FOR SIGNAL AMPLIFICATION OF SURFACE ACOUSTIC WAVE ELEMENT

CROSS-REFERENCE TO RELATED APPLICATION

This application claims priority to Korean Patent Application No. 10-2008-0110553, filed on Nov. 7, 2008, and all the benefits accruing therefrom under 35 U.S.C. §119, the contents of which in its entirety are herein incorporated by reference.

BACKGROUND

1. Field

Exemplary embodiments relate to a surface acoustic wave ("SAW") device and a method for signal amplification of a SAW element, and more particularly to a SAW device for amplifying a signal of a SAW element using a luminescence material and a method for signal amplification of the SAW element.

2. Description of the Related Art

A SAW sensor having a SAW element may be used for detecting a target material in a sample using a piezoelectric material. An oscillation signal may be applied to the SAW sensor. The oscillation signal may be converted into a SAW, or a SAW may be converted into an oscillation signal through an interdigital transducer ("IDT") electrode included in the SAW sensor.

Meanwhile, if the target material existing in the sample is bound on the surface of the SAW sensor, the surface mass of the sensor may be changed due to the material. The change of surface mass may cause a change of a SAW generated by the IDT electrode. Thus, the target material may be quantitatively and qualitatively analyzed by comparing an output of the SAW sensor bound to the target material with an output of a reference element to which the target material is not bound.

SUMMARY

In an exemplary embodiment, there is provided a surface acoustic wave ("SAW") device capable of amplifying a signal of a SAW element bound to a target material by using a luminescence material bound to the target material, and a method for signal amplification of the SAW element.

In another exemplary embodiment, there is provided a SAW device including a SAW element; a first material fixed on the SAW element and binding to a target material in a sample; a luminescence material bound to the target material; and a light source for applying light to the luminescence material.

In another exemplary embodiment, there is provided a method for signal amplification of a SAW element, including providing a SAW element having a first material formed on a surface thereof; binding a target material in a sample to the first material; and applying light to a luminescence material bound to the target material.

BRIEF DESCRIPTION OF THE DRAWINGS

The above and other aspects, features and advantages of the disclosed exemplary embodiments will be more apparent from the following detailed description taken in conjunction with the accompanying drawings in which:

FIG. 1A is a sectional view showing an exemplary embodiment of a surface acoustic wave ("SAW") device;

FIG. 1B is a sectional view showing an exemplary embodiment of a SAW device;

FIG. 2A is a plan view showing a SAW element shown in FIG. 1;

FIG. 2B is a side view showing the SAW element shown in FIG. 1;

FIG. 3A is a sectional view showing an exemplary embodiment of a SAW device;

FIG. 3B is a sectional view showing an exemplary embodiment of a SAW device;

FIG. 3C is a sectional view showing an exemplary embodiment of a SAW device;

FIG. 4 is a flowchart illustrating an exemplary embodiment of a method for signal amplification of a SAW element;

FIG. 5 is a time-series graph showing an oscillation frequency of a SAW element to which a luminescence material is not bound in comparison to an oscillation frequency of a reference element; and FIG. 6 is a time-series graph showing an oscillation frequency of a SAW element to which a luminescence material is bound according to an exemplary embodiment in comparison to an oscillation frequency of a reference element.

DETAILED DESCRIPTION

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. do not denote a limitation of quantity, but rather denote the presence of at least one of the referenced item. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

Figure 1A:
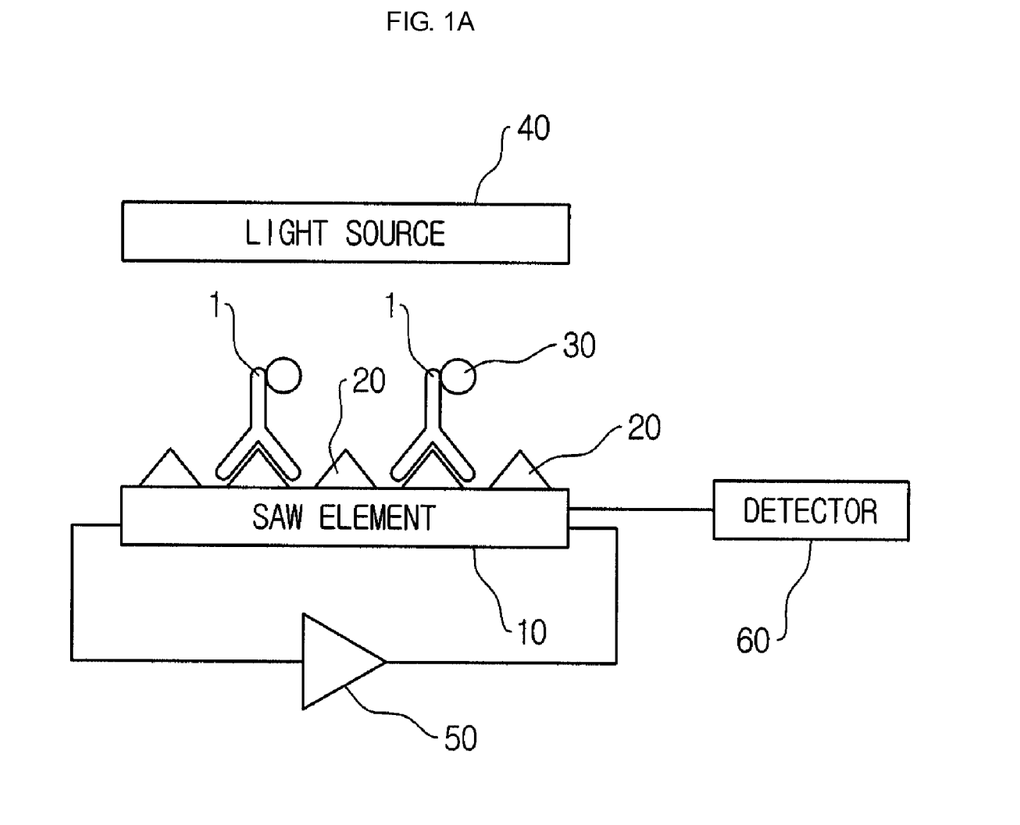

FIG. 1A is a sectional view showing an exemplary embodiment of a surface acoustic wave ("SAW") device.

Referring to FIG. 1A, the SAW device may include a SAW element 10, a first material 20, a luminescence material 30 and a light source 40.

The SAW element 10 may generate a SAW, which is a mechanical wave, using an oscillation signal that is an electric signal. The generated SAW may be propagated along the surface of the SAW element 10. At this time, the SAW element 10 may be exposed to a sample including a target material 1. The SAW generated by the SAW element 10 may be influenced by the target material 1 bound to the SAW element 10. Meanwhile, the SAW element 10 may convert the SAW into an electric signal again and then output the electric signal. Configurations and functions of the SAW element 10 will be explained later in detail with reference to FIG. 2.

In another exemplary embodiment, the signal output from the SAW element 10 may be input again to the SAW element 10 using an oscillator 50 such that an oscillation signal may be applied to the SAW element 10. Alternatively, in another exemplary embodiment, an oscillation signal may be generated by a signal generator and then applied to the SAW element 10.

The signal output from the SAW element 10 may be detected by a detector 60. The output signal of the SAW element 10 may be influenced by surface mass or temperature of the SAW element 10, and viscosity, density or conductivity of the sample to which the SAW element 10 is exposed. The detector 60 may analyze the target material 1 in the sample by comparing the output signal of the SAW element 10 bound to the target material 1 with an output signal of a reference element (not shown) to which the target material 1 is not bound.

The first material 20 may be fixed on the surface of the SAW element 10. The first material 20 may be specifically bound to the target material 1 within the sample. Namely, the first material 20 may function as a receptor of the target material 1.

In an exemplary embodiment, the first material 20 may include at least one of protein, DNA, RNA, cell, aptamer and polymer. For example, the target material 1 may be an antibody (e.g., IgG, IgA, IgM etc.) as shown in FIG. 1A. In this case, the fist material 20 and the target material 1 may be bound to each other through an antigen-antibody reaction.

Figure 1B:
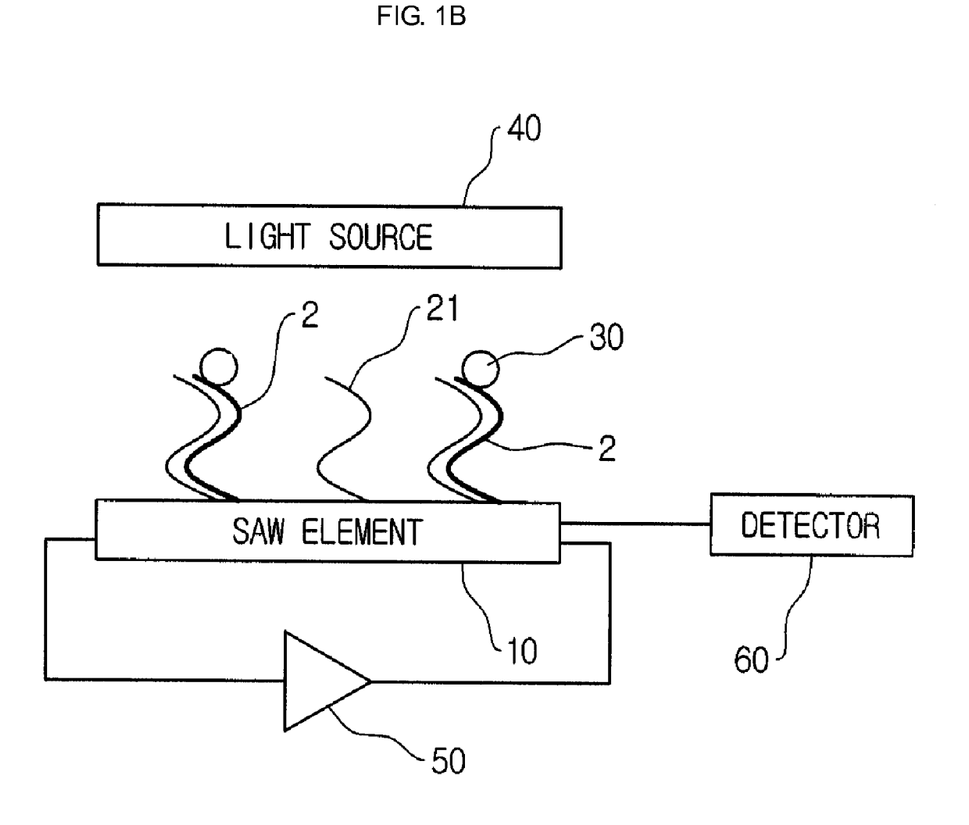

Meanwhile, referring to FIG. 1B, in another exemplary embodiment, the first material 21 may be DNA or RNA. In this case, a target material 2 having a sequence corresponding to the sequence of the first material 21 may be bound to the first material 21.

The target material 1 may include a luminescence material 30 bound to a portion of the target material 1. And, the light source 40 may apply light to the luminescence material 30.

If a light of a specific wavelength is applied to the luminescence material 30, particles such as electrons or ions may be accelerated due to the energy transferred from the light. At this time, by means of the accelerated particles, an electric field around the particles may be emitted in a form of an electromagnetic wave.

The luminescence material 30 may be classified as a fluorescence material and a phosphorescence material depending on the path along which the accelerated particle loses its energy. In an exemplary embodiment, the luminescence material 30 may include at least one of quinine, fluorescein, rohdamine B, anthracene, pyrene and cyanine.

If the electromagnetic wave emitted as explained above reaches the SAW element 10, changes in electric charges and energy may be induced on the surface of the SAW element 10, which may amplify the SAW. Thus, it is possible to amplify a signal output from the SAW element 10.

Meanwhile, the light source 40 may be a unit for applying a light of a predetermined wavelength to excite particles included in the luminescence material 30. For example, in case a cyanine-based material Cy3 is used as the luminescence material 30, the light source 40 may apply light with a wavelength of about 550 nm to the luminescence material 30 so as to generate an electromagnetic wave from the luminescence material 30.

In an exemplary embodiment, the light source 40 may include a light emitting diode ("LED"). When light is applied to the luminescence material 30 using an LED, less heat is generated than when a laser is used, so it is possible to prevent the signal of the SAW element 10 from being distorted by heat.

The SAW device as explained above may amplify an output signal of the SAW element 10 using an electromagnetic wave generated by applying light to the luminescence material 30. Since the luminescence material 30 is bound to the target material 1, a signal difference between the SAW element 10 bound to the target material 1 and a reference device not bound to the target material 1 is increased. Thus, it becomes easy to analyze the target material 1 using the SAW element 10.

Figure 2A:
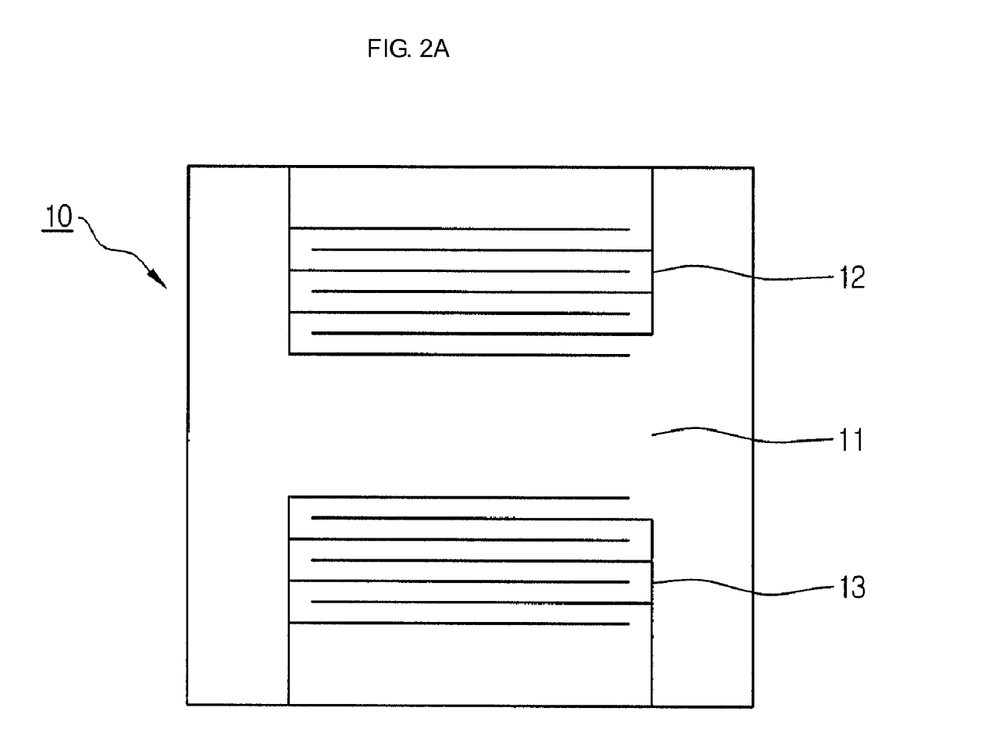
Figure 2B:
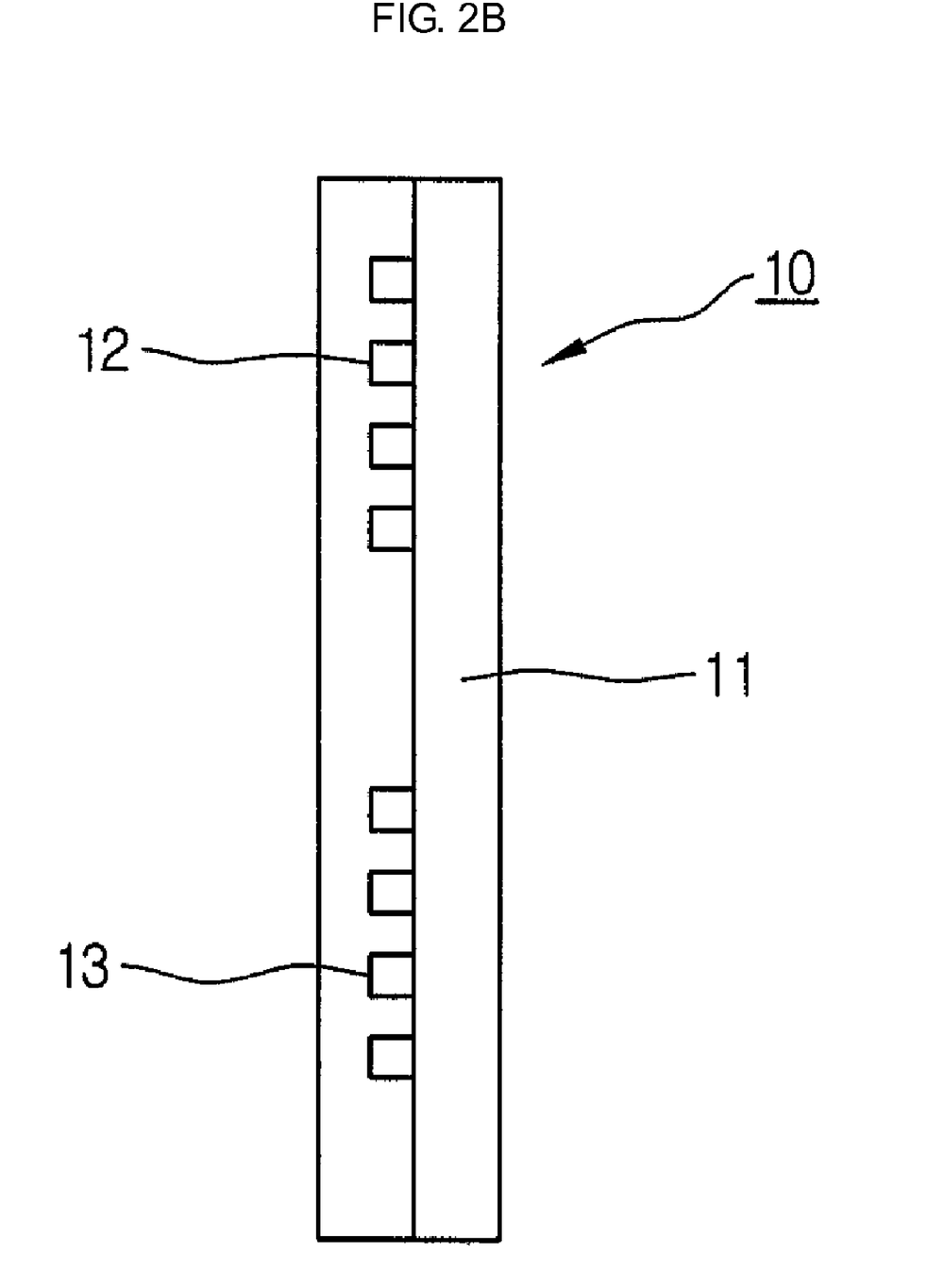

FIG. 2A is a plan view showing a detailed configuration of the SAW element 10 shown in FIG. 1, and FIG. 2B is a side view of the SAW element 10.

Referring to FIGS. 2A and 2B, the SAW element 10 may include a substrate 11, an input electrode 12 and an output electrode 13.

In an exemplary embodiment, the input electrode 12 and the output electrode 13 may be interdigital transducer ("IDT") electrodes that include comb-type electrodes facing each other. Also, the input electrode 12 and the output electrode 13 may be made of a metal or an alloy. For example, the input electrode 12 and the output electrode 13 may be made of aluminum (Al) or silver (Ag).

An oscillation signal may be applied to electrodes that compose the input electrode 12. If an oscillation signal is applied, a mechanical wave, namely a SAW, may be generated at a portion where the input electrode 12 and the substrate 11 contact each other. The SAW may be propagated toward the output electrode 13 along the surface of the substrate 11.

In an exemplary embodiment, the substrate 11 may be made of a piezoelectric material that is suitable for generating and propagating a SAW. For example, the substrate 11 may be made of a single crystal piezoelectric material such as quartz, lithium tantalite and lithium niobate, or a piezoelectric ceramic such as lead zirconate titanate ("PZT") ceramic.

The SAW generated by the input electrode 12 may be propagated along the surface of the substrate 11. The SAW propagated along the substrate 11 may be transferred to the output electrode 13 positioned at a location spaced apart from the input electrode 12. If the SAW is transferred to the output electrode 13, the SAW may be converted into an electric signal again at a portion where the substrate 11 made of piezoelectric material contacts with the output electrode 13.

As described above, the SAW generated by the SAW element 10 may be influenced by a mass change caused by the target material bound to the surface of the SAW element 10. Thus, the target material may be analyzed by comparing an output signal of the SAW element 10 bound to the target material with an output signal from a reference element not having the target material bound to it.

In an exemplary embodiment, the SAW generated by the SAW element 10 may be amplified by inducing electric charge or energy change on the surface of the SAW element 10 by the electromagnetic wave, besides a mass change. The luminescence material is bound only to a specific target material. Thus, in case the SAW is amplified using an electromagnetic wave, signal distortion is not made by factors other than the target material. As a result, accurate measurement may be ensured.

The SAW element 10 shown in FIGS. 2A and 2B is an example of the SAW sensor. Thus, in other exemplary embodiments, SAW elements with different configurations may be used, and also SAW elements having a usage other than as a sensor may also be used.

Figure 3A:
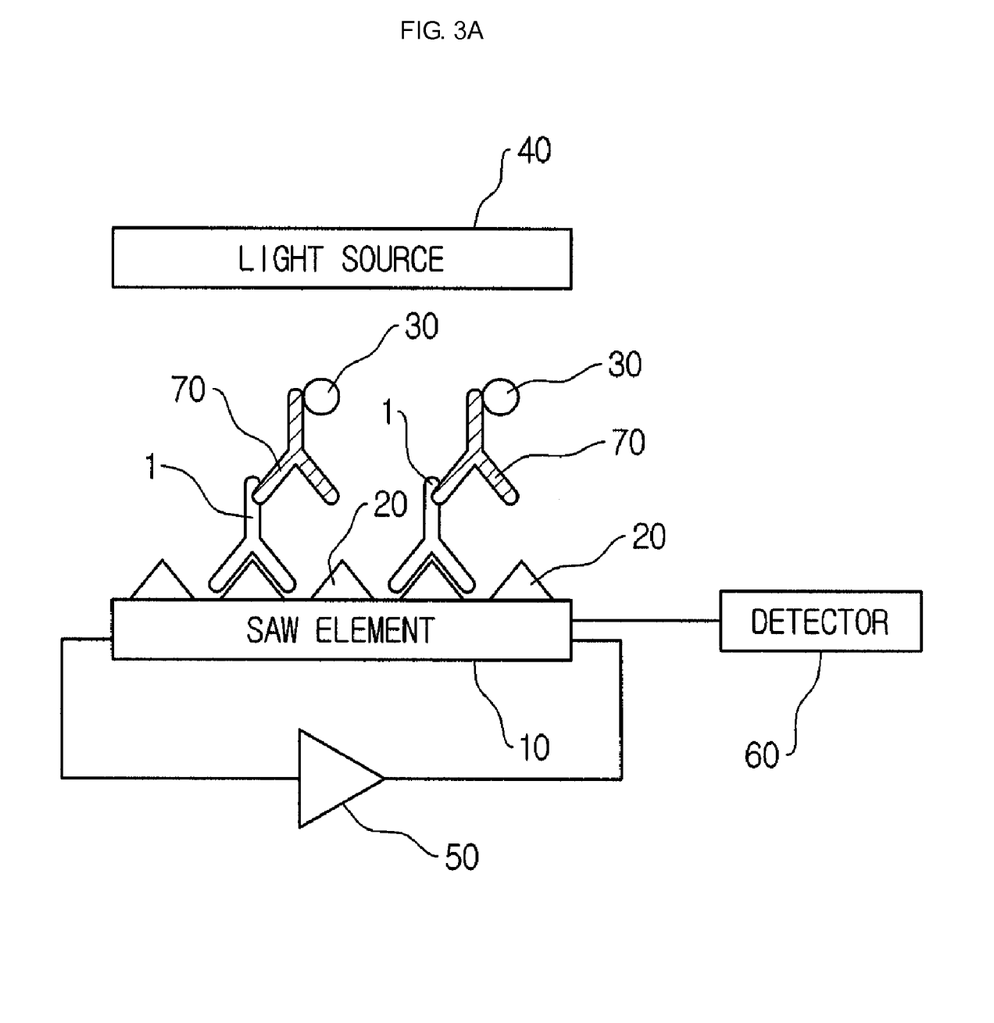

FIG. 3A is a sectional view showing an exemplary embodiment of a SAW device.

Referring to FIG. 3A, the SAW device may include a SAW element 10, a first material 20, a luminescence material 30, a light source 40 and a second material 70. Configurations and operations of the SAW element 10, the first material 20 and the light source 40 may be substantially identical to those of the exemplary embodiment explained with reference to FIG. 1. Therefore, detailed explanation thereof will be omitted for brevity.

Meanwhile, in FIG. 3A, the luminescence material 30 may be bound to the second material 70 instead of the target material 1, and the second material 70 may be bound to the target material 1. For example, in an exemplary embodiment, the target material 1 may be an antibody, and the second material 70 may be a secondary antibody binding to the target material 1.

In another exemplary embodiment, the second material 70 may include at least one of protein, DNA, RNA, cell, aptamer and polymer. For example, the second material 70 may be an antibody (e.g., IgG, IgA, IgM, etc.) as shown in FIG. 3A.

If light is applied by the light source 40 in the SAW device configured as above, an electromagnetic wave is generated from the luminescence material 30. The electromagnetic wave may amplify a signal of the SAW element 10, as explained above.

Figure 3B:
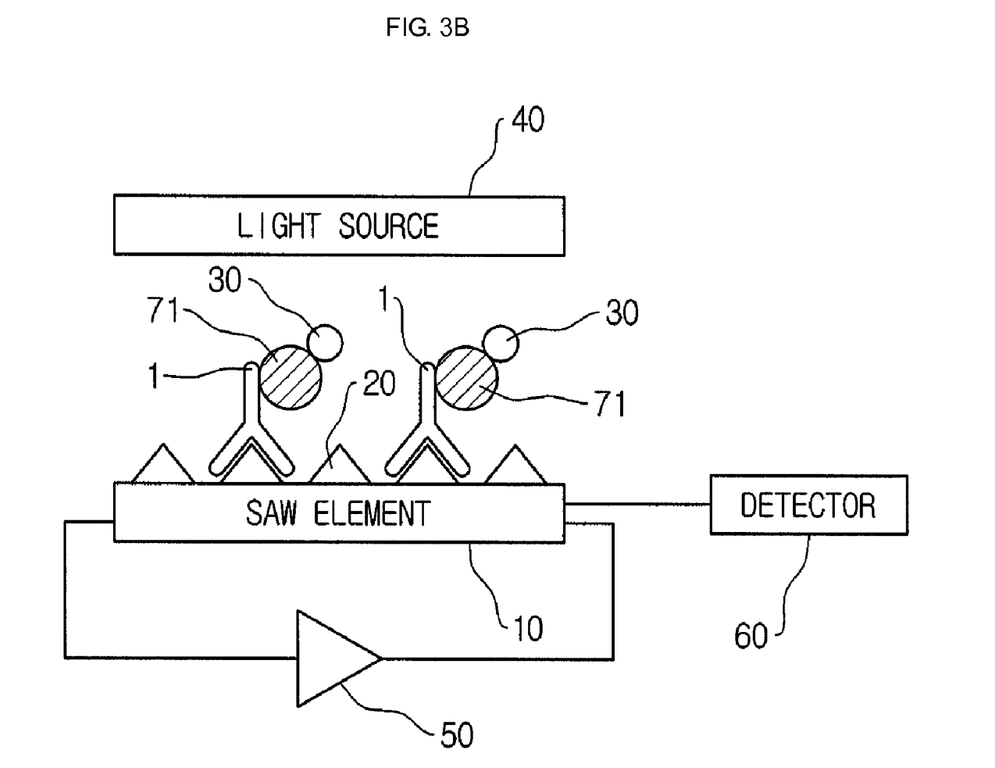

Meanwhile, in another exemplary embodiment, the target material 1 may be an antibody, and the second material 71 may be a receptor, as shown in FIG. 3B. At this time, the second material 71 may be a material binding to a region other than the Fv region of the target material 1 that is an antibody. For example, the second material 71 may include at least one of a protein A, a protein B and an aptamer.

Figure 3C:
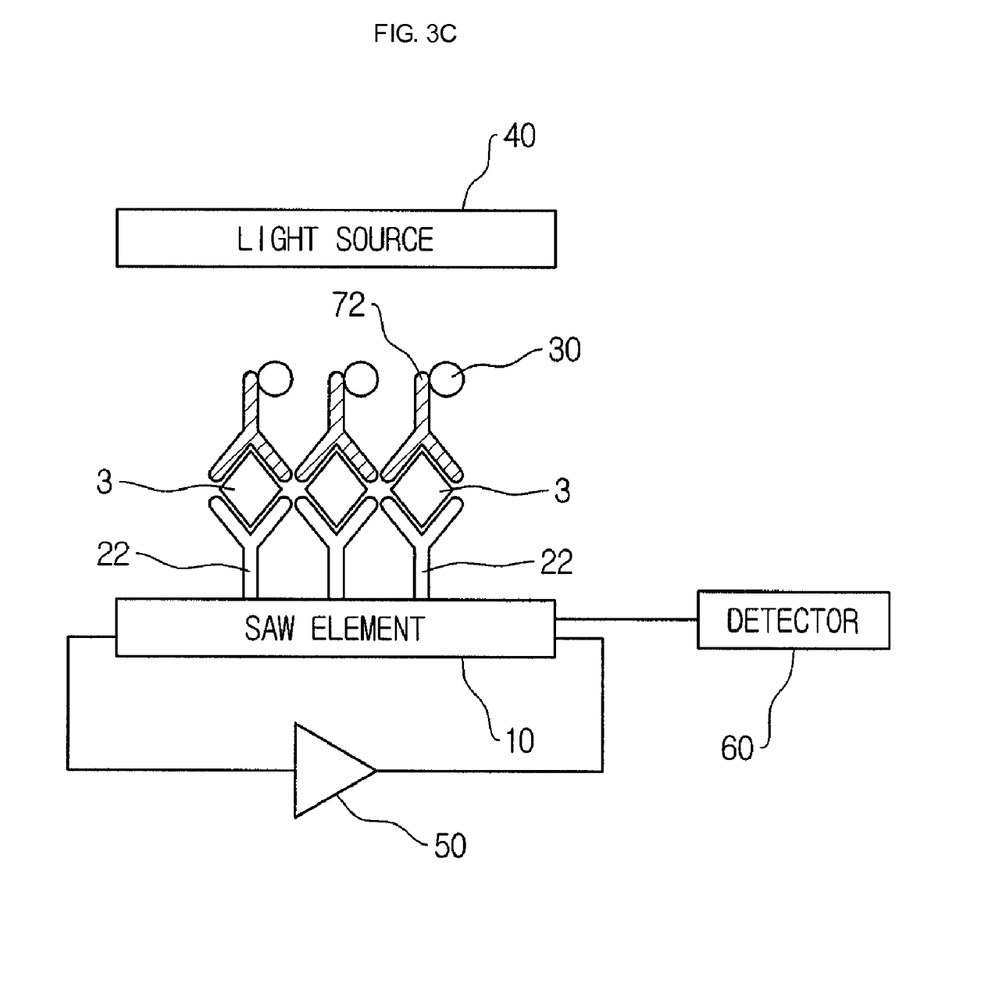

Meanwhile, in another exemplary embodiment, the target material 3 may be an antigen, and the first and second materials 22, 72 may be antibodies, respectively, as shown in FIG. 3C. That is, the first material 22 may function as an antibody as well as a receptor of the target material 3, and the second material 72 may function as a secondary antibody. The luminescence material 30 may be bound to the second material 72.

Figure 4:
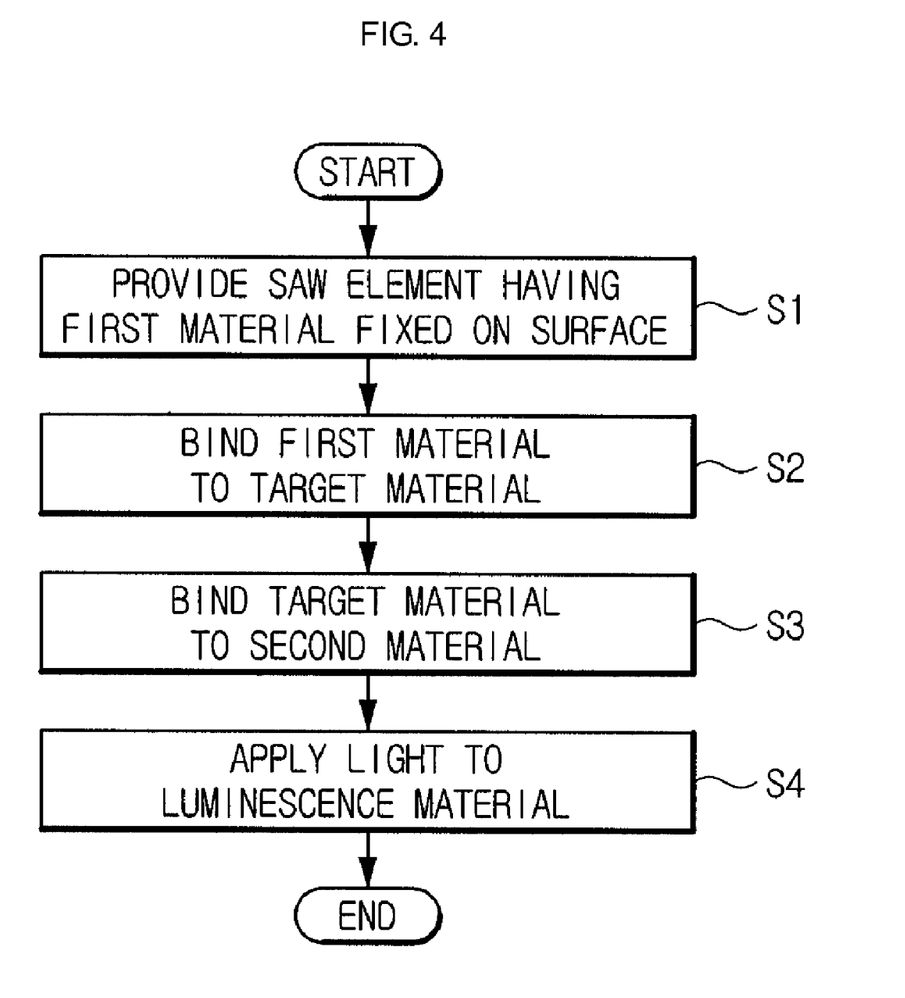

FIG. 4 is a flowchart illustrating an exemplary embodiment of a method for signal amplification of a SAW element.

First, the method for signal amplification of a SAW element may include providing a SAW element (S1). A first material may be fixed on a surface of the SAW element.

Then, the first material may be bound to a target material (S2). For this purpose, the first material may be made of a substance that is specifically bound to the target material within a sample. Namely, the first material may function as a receptor of the target material. In an exemplary embodiment, the first material may include at least one of protein, DNA, RNA, cell, aptamer and polymer. For example, the first material may be an antibody.

Then, a second material may be bound to the target material (S3). The second material may be partially bound to a luminescence material. The luminescence material may be labeled to the second material by means of various physical or chemical bonding.

Meanwhile, in another exemplary embodiment, a luminescence material may be labeled to the target material itself. In this case, since the luminescence material is directly bound to the target material, the process S3 for binding the second material bound to a luminescence material to the target material may be omitted.

Then, light may be applied to the luminescence material bound to the target material directly or by way of the second material (S4). If light is applied, particles such as electrons or ions included in the luminescence material may be accelerated by the energy applied from the light. At this time, due to the accelerated particles, an electric field may be emitted around the particles in a form of electromagnetic wave.

The electromagnetic wave generated by the luminescence material may amplify an output signal of the SAW element. Since the output signal of the SAW element bound to the target material is amplified, the amplified signal may be compared with a signal of a reference element not bound to the target material in an easier way. Also, signal distortion caused by factors other than the target material may be excluded.

Figure 5:
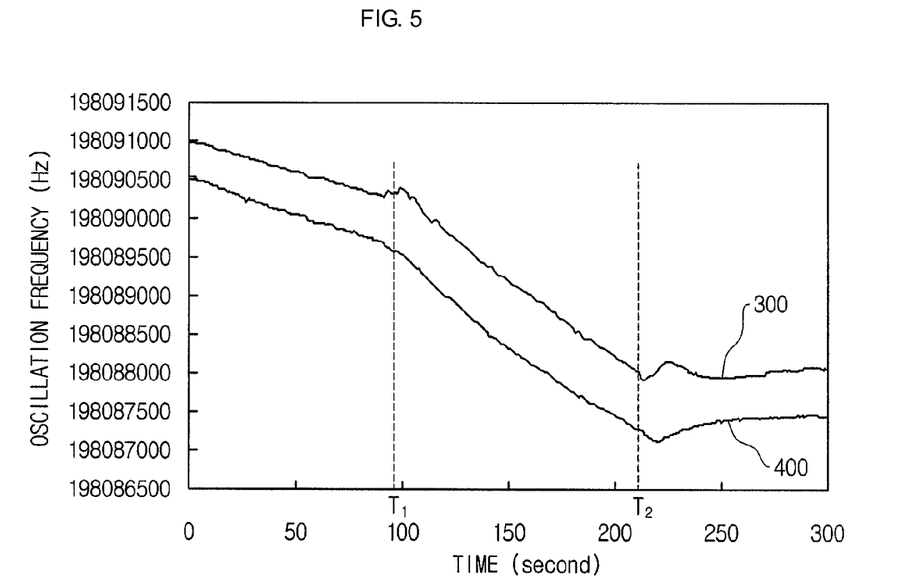

FIG. 5 is a time-series graph showing an oscillation frequency of a SAW element to which a luminescence material is not bound in comparison to an oscillation frequency of a reference element.

The two graphs shown in FIG. 5 respectively represent an oscillation frequency 300 of a reference element and an oscillation frequency 400 of the SAW element bound to the target material in time series. Compared with the oscillation frequency 300 of a reference element, it could be found that the oscillation frequency 400 of the SAW element bound to the target material is decreased due to the influence of the target material.

Time $T_1$ represents a time when application of light begins, and time $T_2$ represents a time when application of light is stopped. Since the SAW element is not bound to the target material, a difference between the oscillation frequency 300 of the reference element and the oscillation frequency 400 of the SAW element bound to the target material is constant even in the time interval between $T_1$ and $T_2$ during which light is applied. In the time interval between $T_1$ and $T_2$, the oscillation frequencies 300, 400 of both elements are decreased resulting from a temperature change caused by the light, so the difference between both oscillation frequencies 300, 400 is not changed.

Figure 6:
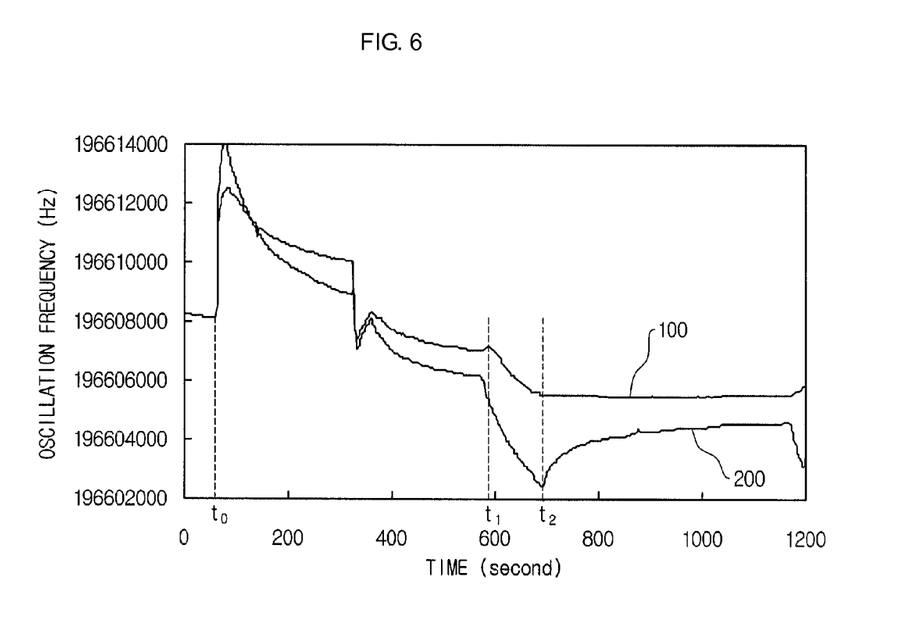

FIG. 6 is a time-series graph showing an oscillation frequency of a SAW element to which a luminescence material is bound according to an exemplary embodiment in comparison to an oscillation frequency of a reference element.

Two graphs are shown in FIG. 6, which respectively illustrate an oscillation frequency 100 of a reference device and an oscillation frequency 200 of the SAW element bound to the target material in time series. Compared with the oscillation frequency 100 of the reference element, it could be found that the oscillation frequency 200 of the SAW element bound to the target material is decreased due to the influence by the target material. Thus, the target material may be analyzed from the difference of oscillation frequencies.

In FIG. 6, time $t_0$ represents a time when the SAW element begins to be exposed to a sample including the target material. Meanwhile, time $t_1$ represents a time when application of light begins, and time $t_2$ represents a time when the application of light is stopped. As shown in FIG. 6, a difference between the oscillation frequency 100 of the reference element and the oscillation frequency 200 of the SAW element

What is claimed is:

1. A surface acoustic wave device, comprising:
   a surface acoustic wave element;
   a first material fixed on the surface acoustic wave element and binding to a target material in a sample;
   a luminescence material bound to the target material; and
   a light source configured to apply light to the luminescence material such that the luminescence material produces an electromagnetic wave that amplifies a signal output by the surface acoustic wave element.

2. The surface acoustic wave device according to claim 1, further comprising a second material bound to the target material and the luminescence material, wherein the luminescence material is bound to the target material by way of the second material.

3. The surface acoustic wave device according to claim 2, wherein the second material comprises at least one of a protein, DNA, RNA, a cell, an aptamer and a polymer.

4. The surface acoustic wave device according to claim 3, wherein the second material is an antibody.

5. The surface acoustic wave device according to claim 1, wherein the first material comprises at least one of a protein, DNA, RNA, a cell, an aptamer and a polymer.

6. The surface acoustic wave device according to claim 5, wherein the first material is an antibody.

7. The surface acoustic wave device according to claim 1, wherein the luminescence material comprises at least one of quinine, fluorescein, rohdamine B, anthracene, pyrene and cyanine.

8. The surface acoustic wave device according to claim 1, wherein the light source comprises a light emitting diode.

9. The surface acoustic wave device according to claim 1, further comprising an oscillator configured to receive the signal output by the surface acoustic wave element and to apply an oscillation signal to the surface acoustic wave element.

10. The surface acoustic wave device according to claim 1, further comprising a signal generator configured to apply an oscillation signal to the surface acoustic wave element.

11. The surface acoustic wave device according to claim 1, wherein the luminescence material comprises particles that are accelerated due to energy being transferred from the light to the luminescence material and produce the electromagnetic wave.

12. A method for signal amplification of a surface acoustic wave element, comprising:
   providing the surface acoustic wave element having a first material formed on a surface thereof;
   binding a target material in a sample to the first material; and
   applying light to a luminescence material bound to the target material from a light source such that the luminescence material produces an electromagnetic wave that amplifies a signal output from the surface acoustic wave element.

13. The method for signal amplification of the surface acoustic wave element according to claim 12, further comprising, binding a second material bound to the luminescence material to the target material after binding the target material to the first material.

14. The method for signal amplification of the surface acoustic wave element according to claim 13, wherein the second material comprises at least one of protein, DNA, RNA, cell, aptamer and polymer.

15. The method for signal amplification of the surface acoustic wave element according to claim 14, wherein the second material is an antibody.

16. The method for signal amplification of the surface acoustic wave element according to claim 12, wherein the first material comprises at least one of a protein, DNA, RNA, a cell, an aptamer and a polymer.

17. The method for signal amplification of the surface acoustic wave element according to claim 16, wherein the first material is an antibody.

18. The method for signal amplification of the surface acoustic wave element according to claim 12, wherein the luminescence material comprises at least one of quinine, fluorescein, rohdamine B, anthracene, pyrene and cyanine.

19. The method for signal amplification of the surface acoustic wave element according to claim 12, further comprising receiving the signal output by the surface acoustic wave element at an oscillator and applying an oscillation signal to the surface acoustic wave element utilizing the oscillator.

20. The method for signal amplification of the surface acoustic wave element according to claim 12, wherein the luminescence material comprises particles that are accelerated due to energy being transferred from the light to the luminescence material and produce the electromagnetic wave.

* * * * *